(12) United States Patent
Terry et al.

(10) Patent No.: US 10,548,917 B2
(45) Date of Patent: *Feb. 4, 2020

(54) SUPPLEMENT FOR THE PREVENTION AND TREATMENT OF GASTROINTESTINAL DISTRESS IN HORSES AND OTHER SPECIES

(71) Applicant: Kaeco Group, Inc., Savannah, MO (US)

(72) Inventors: Kelly Terry, Savannah, MO (US); Leon Kratochvil, Savannah, MO (US); James Harless, Papillion, NE (US); Tom Kratochvil, Arlington, NE (US)

(73) Assignee: KAECO Group Inc., Savannah, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/078,909

(22) PCT Filed: May 23, 2017

(86) PCT No.: PCT/US2017/034055
§ 371 (c)(1),
(2) Date: Aug. 22, 2018

(87) PCT Pub. No.: WO2018/147890
PCT Pub. Date: Aug. 16, 2018

(65) Prior Publication Data
US 2019/0037889 A1    Feb. 7, 2019

Related U.S. Application Data

(63) Continuation-in-part of application No. 15/161,689, filed on May 23, 2016, now Pat. No. 9,694,042.

(51) Int. Cl.
| | |
|---|---|
| *A61K 36/22* | (2006.01) |
| *A61K 31/736* | (2006.01) |
| *A61K 31/525* | (2006.01) |
| *A61K 31/51* | (2006.01) |
| *A61K 35/747* | (2015.01) |
| *A61K 31/714* | (2006.01) |
| *A61K 31/685* | (2006.01) |
| *A23K 50/20* | (2016.01) |

(Continued)

(52) U.S. Cl.
CPC ............ *A61K 31/736* (2013.01); *A23K 10/18* (2016.05); *A23K 10/20* (2016.05); *A23K 10/30* (2016.05); *A23K 20/10* (2016.05); *A23K 20/105* (2016.05); *A23K 20/158* (2016.05); *A23K 20/174* (2016.05); *A23K 20/20* (2016.05); *A23K 50/20* (2016.05); *A61K 9/0053* (2013.01); *A61K 9/14* (2013.01); *A61K 31/047* (2013.01); *A61K 31/198* (2013.01); *A61K 31/352* (2013.01); *A61K 31/355* (2013.01); *A61K 31/4188* (2013.01); *A61K 31/4415* (2013.01); *A61K 31/455* (2013.01); *A61K 31/51* (2013.01); *A61K 31/525* (2013.01); *A61K 31/685* (2013.01); *A61K 31/702* (2013.01); *A61K 31/714* (2013.01); *A61K 33/04* (2013.01); *A61K 33/30* (2013.01); *A61K 35/744* (2013.01); *A61K 35/747* (2013.01); *A61K 36/22* (2013.01); *A23V 2002/00* (2013.01); *A23V 2200/222* (2013.01); *A23V 2200/3204* (2013.01); *A23V 2250/0632* (2013.01); *A23V 2250/1626* (2013.01); *A23V 2250/1642* (2013.01); *A23V 2250/1842* (2013.01); *A23V 2250/502* (2013.01); *A23V 2250/5114* (2013.01); *A23V 2250/641* (2013.01); *A23V 2250/706* (2013.01); *A23V 2250/712* (2013.01); *A23V 2250/72* (2013.01); *A23Y 2220/03* (2013.01); *A23Y 2220/17* (2013.01); *A23Y 2220/67* (2013.01); *A61K 2300/00* (2013.01)

(58) Field of Classification Search
None
See application file for complete search history.

(56) References Cited

U.S. PATENT DOCUMENTS

| | | | |
|---|---|---|---|
| 7,824,706 B2 | 11/2010 | Bedding et al. | |
| 9,694,042 B1 * | 7/2017 | Terry | A23K 20/158 |

(Continued)

FOREIGN PATENT DOCUMENTS

| | | | |
|---|---|---|---|
| CN | 102688273 | * | 9/2012 |
| CN | 102688273 A | | 9/2012 |

(Continued)

OTHER PUBLICATIONS

Gortzi O. et al. Study of Antioxidant and Antimicrobial Activity of Chios Mastic Gum . . . J Food Processing & Technology 5(8) 1000355/1-5. 2014 (Year: 2014).*

(Continued)

*Primary Examiner* — Ralph J Gitomer
(74) *Attorney, Agent, or Firm* — Gregory L. Porter; Hunton Andrews Kurth LLP

(57) ABSTRACT

Embodiments of a method and supplement for preventing and/or treating gastrointestinal distress, including ulcer conditions, in animals are disclosed. The supplement comprises mastic gum and an emulsifying agent such as lecithin. The supplement may also comprise B vitamins, one or more prebiotics or probiotics, and one or more minerals as well as, pH buffers and flavoring. A disclosed method of preventing and/or treating gastrointestinal distress comprises orally dosing an animal with the supplement at least one daily.

11 Claims, 1 Drawing Sheet

(51) Int. Cl.

| | | |
|---|---|---|
| A23K 10/30 | (2016.01) | |
| A23K 20/158 | (2016.01) | |
| A61K 9/00 | (2006.01) | |
| A23K 20/10 | (2016.01) | |
| A23K 20/20 | (2016.01) | |
| A23K 20/174 | (2016.01) | |
| A23K 10/18 | (2016.01) | |
| A61K 31/4415 | (2006.01) | |
| A61K 31/702 | (2006.01) | |
| A61K 31/4188 | (2006.01) | |
| A61K 9/14 | (2006.01) | |
| A61K 31/355 | (2006.01) | |
| A61K 33/04 | (2006.01) | |
| A23K 10/20 | (2016.01) | |
| A23K 20/105 | (2016.01) | |
| A61K 35/744 | (2015.01) | |
| A61K 31/198 | (2006.01) | |
| A61K 31/047 | (2006.01) | |
| A61K 31/455 | (2006.01) | |
| A61K 33/30 | (2006.01) | |
| A61K 31/352 | (2006.01) | |

(56) References Cited

U.S. PATENT DOCUMENTS

| | | | | |
|---|---|---|---|---|
| 9,993,498 | B2 * | 6/2018 | Terry | A23K 20/158 |
| 2003/0175307 | A1 * | 9/2003 | Garner | A61K 35/741 |
| | | | | 424/234.1 |
| 2005/0238731 | A1 * | 10/2005 | Holt | A61K 31/07 |
| | | | | 424/643 |
| 2008/0038370 | A1 | 2/2008 | Holt | |
| 2009/0252827 | A1 * | 10/2009 | Baginski | A61K 36/48 |
| | | | | 426/2 |
| 2015/0104424 | A1 * | 4/2015 | Scivoletto | A61K 36/22 |
| | | | | 424/93.4 |
| 2019/0046559 | A1 * | 2/2019 | Terry | A61K 31/4188 |

FOREIGN PATENT DOCUMENTS

| | | | |
|---|---|---|---|
| JP | 2003 137797 | * | 5/2003 |
| JP | 2003137797 A | | 5/2003 |
| KR | 2001 069608 | * | 7/2001 |
| KR | 2009 0131585 A | * | 12/2009 |
| KR | 20090131585 A | | 12/2009 |

OTHER PUBLICATIONS

Advertisement for "Equine Intact Liquid", Intact Nutrition, retrieved from http://www.intactnutrition.com/view-product/equine-intact-liquid (Mar. 12, 2016).
Advertisement for "Starting Gate Nutritional Granules", SBS Equine—Shoe Bond Systems, Inc., retrieved from http://sbsequine.com/starting-gate-nutritional-granules/ (Mar. 9, 2016.
Advertisement for "Gastromax", retrieved from http://www.unitedvetequine.com/horse-digsetion/GastroMax3-horse-ulcer-prevention.asp (Mar. 4, 2016).
Advertisement for Gastro-Plex (Pellets), retrieved from https://www.smartpakequine.com/ps/gastroplex-pellets-13348 (Mar. 9, 2016).
"Equine Ulcer Medications & Gastric Health Supplements", retrieved from https://www.smartpakequine.com/equine-ulcer-medications-and-gastric-health-supplements-24pc.
"FDA Issues Warning Letters for Unapproved Omeprazole Drugs Marketed for Use in Ulcers", FDA, Center for Veterinary Medicine, retrieved from https://www.fda.gov/Animal/Veterinary/NewsEvents/CVMUpdates/ucm422694.htm (Mar. 4, 2016).
"Chios Mastiha Gum Resin for Equine Gastric Ulcers", retrieved from http://www.gravelproofhoof.org/#!mastiha=gum/ctjy (Mar. 12, 2016).
Advertisement for "Fantastic Mastic", Healing Bliss Botanicals, retrieved from http://www.healingbliss.ca/blogs/news/3852852-fantastic-mastic (Feb. 17, 2016).
"Equine Gastric Ulcer Syndrome", retrieved from http://www.scott-dunns.co.uk/equine_gastric_ulceration.htm (Feb. 17, 2016).
Advertisement—Your Horse Ulcer-Free Pt. 3—"Colonic Ulcers in the Hindgut", retrieved from http://www.succeed-equine.com/succeed-blog/2010/11/18/your-horse-ulcer-free-pt-3-colo (Aug. 28, 2014).
Advertisement—Your Horse Ulcer-Free Pt. 5—"Euqine Ulcer Treatments", retrieved from http://www.succeed-equine.com/succeed-blog/2010/11/18/your-horse-ulcer-free-pt-5-equi (Aug. 28, 2014).
Advertisement—Your Horse Ulcer-Free Pt. 6—"Preventing Equine Ulcers", retrieved from http://www.succeed-equine.com/succeed-blog/2010/03/03/your-horse-ulcer-free-pt-6-prev (Aug. 28, 2014).
Publication—"EndurExtra High Fat for Horses—25 Lbs", Kentucky Performance (Feb. 2, 2012).
"Gastric Ulcers", retrieved from http://www.equisearch.com.article.eqhorseulc217 (Aug. 28, 2014).
"Chios Mastiha Gum Resin for Equine Gastric Ulcers", retrieved from http://www.gravelproofhoot.org/ (Dec. 29, 2014).
Excerpt of article—"Is Chios Mastic Used by Humans?", retrieved from http://imtelligenthorsecare.co.uk/product/chios-mastic-resin (Dec. 29, 2014).
"Chios Mastiha Gum Resin for Equine Gastric Ulcers", rertrieved from http://www.gravelproofhoot.org/ (Dec. 22, 2014).
"Ulcers: Is Mastic Gum the Breakthrough in Ulcer Treatment?", retrieved from http://www.health4youonline.com/PBCPPlayer.asp?ID=1342521 (Aug. 22, 2014_.
Advertisement—Mastic Gum Mastic Gum Resin, retrieved from http://www.calmhealthyhorses.com/product_nz/masticgum.html (Dec. 29, 2014).
"Does mastic gum cure H.Pylori", retrieved form https://answers.yahoo.com/question/Index?qid-20060803111334bxFTm *08/06/20014.
"Mastic Gum Kills Helicobacter pylori", retrieved from http://www.nejm.org/doi/full/10/1056/NEJM1998/12243392618.
"Peptic Ulcers can be easily and quickly treated with antibiotics?", retrieved from http://hsionline.com/2009/06/15/mastic-gum/ (Aug. 5, 2016).
"Diagnosing and Treating Gastric Ulcers in Horses", CEH Horse Report, School of Veterinary Medicine, Univ.Cal. Davis (Oct. 2012).
Advertisement—"Natural Treatment for Gastric Ulcers in Horses", retrieved from http://sbsequine.com/natural-treatment-for-gastric-ulcers-in-horses (Apr. 7, 2014).
"Mastic", retrieved from http://www.drugs.com/npp/mastic.html (Nov. 5, 2015).
"AEC : Ulcergard v. Gastrogard—Which one do I use?", retrieved from http://www.atlantaequine.com/pages/ulcergard_gastrogard.html.
Merial Labeling Information—Gastrogard (omeprazole) Oral Paste for Equine Ulcers (2000).
Advertisement—"Your Horse Ulcer-Free Pt. 2—Equine Gastric Ulcers", retrieved from http://www.succeed-equine.com/succeed-blog/2010/11/18/your-horse-ulcer-free-pt-2-equi (Aug. 28, 2014).
Shakalis, "Equine Gastric Ulcers: A Real Porblem with a Natural Solution", sbsequine.com Lec D-56 (Mar. 2002).
Gortzi et al., "Study of Antioxidant and Antimicrobial Activity of Chios Mastic Gum Fractions . . . ", 5(8)1-5 J. Food Proc & Technol. (Aug. 2014).

* cited by examiner

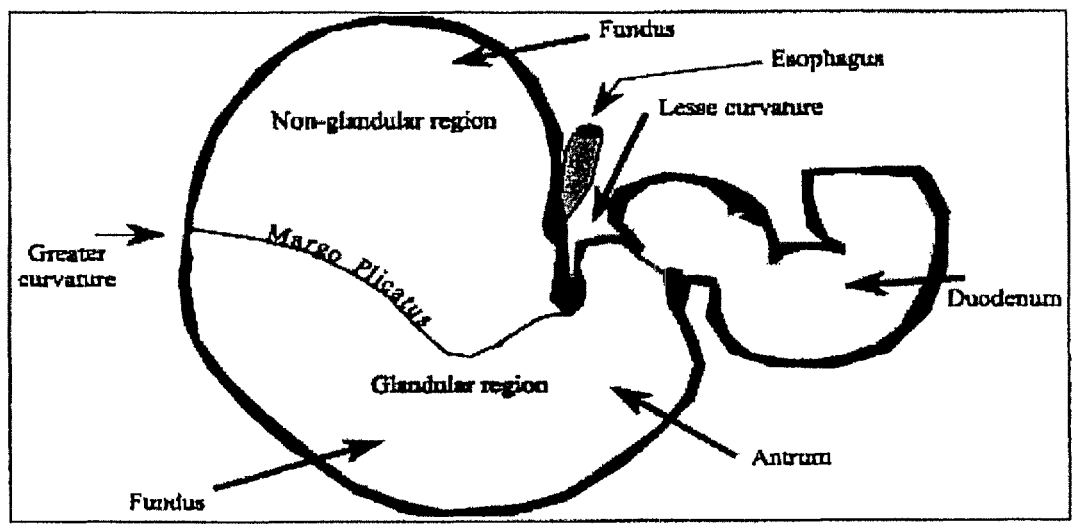
Equine stomach diagram

SUPPLEMENT FOR THE PREVENTION AND TREATMENT OF GASTROINTESTINAL DISTRESS IN HORSES AND OTHER SPECIES

CROSS-REFERENCE TO RELATED APPLICATIONS

This application is a continuation of pending International Application No. PCT/US2017/034055, filed May 23, 2017, which is a continuation-in-part of U.S. Ser. No. 15/161,689, filed May 23, 2016, which granted as U.S. Pat. No. 9,694,042 on Jul. 4, 2017. This application is also related to U.S. Ser. No. 15/388,425, filed Dec. 22, 2016, which granted as U.S. Pat. No. 9,993,498 on Jun. 12, 2018.

FIELD

Embodiments described herein are related to a nutritional supplement for the treatment and/or prevention of gastrointestinal distress in horses and other species of animals.

BACKGROUND AND SUMMARY OF THE INVENTION

The horse is a roaming animal with a gastro intestinal digestive system designed for and accustomed to grazing up to 17 hours a day. Thus, the horse's digestive system is specifically designed for the intake of small quantities of feed over long periods of time. Horses and certain other animals did not evolve to develop the mechanism which turns stomach acid on and off, like humans. Therefore, a horse's stomach typically produces stomach acid 24 hours a day even when there is no food present and such production can be up to 9 gallons of acidic fluid per day.

Stalled horses, with minimal access to pasture for grazing, are normally fed 2-3 times per day which leads to the buildup of excess stomach acid, as the stomach is subjected to prolonged periods of time without feed present to neutralize the acid. As such, gastric ulcers are quite common in domesticated/stalled horses and foals; their prevalence has been estimated at from about 50% to about 90%, depending upon the population surveyed and type and level of athletic activity in which the horses are engaged.

Foals are often subject to stomach ulcers causing morbidity and mortality. Clinical signs of ulcers in foals include intermittent colic (after suckling or eating), frequent recumbency (this is common in foals since this position seems to provide some relief from severe gastric ulceration), intermittent nursing, diarrhea, poor appetite, grinding of teeth and excessive salivation.

Adult horses with stomach ulcers may exhibit one or more clinical signs of ulcers including: poor appetite, attitude changes, decreased performance, reluctance to train or work, excessive recumbency, poor body condition, rough hair coat, weight loss, low grade colic and/or loose feces. More serious cases will show abdominal pain (colic) and/or grinding of the teeth. Others may walk away from food for a period of time as if the horse experiences discomfort when the food first contacts the stomach. Due to the range of common clinical signs of ulcers (and the fact that some horses with ulcers show no outward signs), the only clinically proven way to diagnose and verify stomach ulcers in horses is through gastric endoscopy or gastroscopy. Unfortunately, this involves placing an endoscope into the horse's stomach to examine its inner surface. This is unpleasant for the horse and sometimes a complex procedure for the veterinarian as it invariably requires anesthesia. In addition, this process can be very costly for the horse owner and a large number of veterinarians do not have access to an endoscope; due to the high cost basis for this type of equipment.

Unfortunately, currently available solutions for the prevention or treatment of ulcers or other gastrointestinal distress require a licensed caregiver to prescribe an oral administration of expensive treatments with a dosing syringe. In addition to being costly, many horses or other animals fight this type of treatment, which makes administration difficult.

What is needed is a method and supplement for prevention and/or treatment of gastrointestinal distress, including ulcer conditions in horses and other animal species. It would be further advantageous if the method and supplement employed generally available materials, which were safe and effective. It would be further advantageous if the supplement could be provided in a variety of forms and could be readily formulated with existing equipment. Advantageously, the present invention accomplishes one or more up to all of the aforementioned needs.

In one embodiment, the present invention relates to a nutritional supplement for the prevention or treatment of gastrointestinal distress in animals comprising mastic gum and an emulsifying agent such as lecithin. The supplement may alternatively be used to support a healthy digestive tract in a broad range of animals. In another embodiment, the present invention relates to a method of preventing gastrointestinal distress in an animal comprising: dosing an animal orally at least once daily with a supplement. The supplement comprises: mastic gum and an emulsifying agent such as lecithin in a weight ratio of mastic gum to emulsifying agent such as lecithin of from about 1:10 to about 1:50 based on the total weight of mastic gum and emulsifying agent such as lecithin. In another embodiment, the invention pertains to a method of preventing or treating ulcer conditions in a horse. The method comprises providing an effective amount of a supplement to address and/or treat gastrointestinal distress. The supplement comprises mastic gum, an emulsifying agent such as lecithin, and optionally one or more B vitamins, and one or more biotics selected from prebiotics, probiotics, and combinations thereof.

BRIEF DESCRIPTION OF THE DRAWINGS

FIG. 1 is a diagram of the typical equine stomach.

DETAILED DESCRIPTION

The present invention pertains generally to a nutritional supplement for the prevention or treatment of gastrointestinal distress in animals. It also pertains generally to a method of preventing gastrointestinal distress in an animal and more specifically to a method of preventing or treating ulcer conditions in a horse using a nutritional supplement as described herein.

As used herein "gastrointestinal distress" generally refers to gastrointestinal upset, ulcers, and other digestive conditions or disorders such as diarrhea that are suffered by non-human animals such as a horse, dog, sheep, alpaca, llama, camel, cat, donkey, and cow. In a preferred embodiment, the animal is a horse. The supplements and method described herein may be useful to prevent gastrointestinal distress and/or treat gastrointestinal distress in various animals including pigs, primates, guinea pigs, ferrets, elephants, marine mammals, rabbits, rats, dolphins, tigers, cheetahs, lions zebras, zoo animals, livestock, and domestic animals. Generally, the amount of supplement and/or dosage is higher when the supplements and/or methods are employed to treat as opposed to prevent distress. In certain instances and dosages, the supplements and/or methods may simultaneously treat and prevent further gastrointestinal di stress.

FIG. 1 shows the typical equine digestive tract focusing on the stomach. The equine digestive process can be conceptually divided into the functions carried out in the front of the gastrointestinal tract and those carried out in the back of the GI tract. The functions carried out in the two areas can be very different. In the foregut, after food is gathered up, chewed, and swallowed, the stomach kicks into gear. The main functions of the stomach are to add gastric acid to help with the breakdown of food, to secrete the enzyme pepsinogen to begin protein digestion, and to regulate the passage of food into the small intestine. The stomach can be thought of as a holding and mixing tank, similar to a cement truck that is constantly churning and mixing ingredients.

While food breakdown may begin in the stomach, it continues in the small intestine, where secretions help with the further digestion of protein, simple carbohydrates, and fat. The small intestine is also the main site of nutrient absorption once the food is in small enough form. Amino acids, glucose, vitamins, minerals, and fatty acids are taken into the body as they move along the small intestine, so progress shouldn't be too fast or too slow.

The processes that occur in the hindgut, and particularly in the cecum and colon, are less about breaking down food into smaller, absorbable particles with the aid of enzymes and more about fermenting complex carbohydrates (fiber) into useful end products with the assistance of beneficial organisms. In addition to generating fatty acids, which supply energy or calories, these helpful microorganisms also produce B-vitamins, Vitamin K, and some amino acids. The colon then serves not only to absorb these nutrients but also a portion of the water that accompanies food as it moves along the digestive tract.

Mastic Gum and Emulsifying Agent Such as Lecithin Employed

The nutritional supplement generally comprises a mixture of mastic gum and an emulsifying agent such as lecithin. The types and amounts of mastic gum employed may vary. That is, the specific properties and amounts of the mastic gum that may be employed herein, of course may vary depending upon a number of factors including, for example, the desired results, the animal being treated, as well as the types and amounts of other ingredients employed and the desired form of the supplement.

The mastic gum (a source of triterpenic compounds and phytosterols) may be produced synthetically or, alternatively and more preferably, readily obtained from common natural sources. Mastic gum is sometimes known also as Chios Mastiha. Mastic gum is a natural resin that typically comes from an evergreen small tree or large shrub, which may be cultivated successfully in, for example, the Mediterranean such as the island of Chios, in the Eastern Aegean Sea. This evergreen tree called Schinos, belongs to the family of Pistachia. (Botanical name: *Pistachia Lentiscus* var. *Chia*). Mastic gum useful in the present invention is available commercially from sources such as Parchem or other chemical or nutritional supplement suppliers.

The emulsifying agent or agents employed may vary depending upon a number of factors including, for example, the desired results, the animal being treated as well as the types and amounts of other ingredients employed, and the desired form of the supplement. While not wishing to be bound to any theory it is believed that including a suitable amount of a emulsifying agent may assist in delivery of the mastic gum to the stomach lining by virtue of being at least partially soluble in one or more fats present in the stomach and water. The emulsifying agent may aid in protecting gastric tissue from ulcer injury in, for example, horses and other animals. First, the mastic/emulsifying agent may facilitate forming a barrier between stomach contents and epithelial cells, and second, one or both ingredients may facilitate cell membrane turnover and wound resealing. The emulsifying agent may also assist in partially protecting the mastic gum from being destroyed by excess stomach acid and/or in maintaining an appropriate texture of the mastic gum depending upon the form of the supplement.

Useful emulsifying agents may include any agent that is compatible with mastic gum and relatively non-toxic to normal cells. Such emulsifying agents are often found in food products such as dairy products like ice cream, butter, and margarine, salad dressings, and mayonnaise. Such emulsifying agents are also described in TITLE 21—FOOD AND DRUGS, CHAPTER I—FOOD AND DRUG ADMINISTRATION, DEPARTMENT OF HEALTH AND HUMAN SERVICES, SUBCHAPTER E—ANIMAL DRUGS, FEEDS, AND RELATED PRODUCTS, PART 582 Subpart E—Emulsifying Agents, SUBSTANCES GENERALLY RECOGNIZED AS SAFE and currently include Diacetyl tartaric acid esters of mono- and diglycerides of edible fats or oils, or edible fat-forming fatty acids; Mono- and diglycerides of edible fats or oils, or edible fat-forming acids; Monosodium phosphate derivatives of mono- and diglycerides of edible fats or oils, or edible fat-forming fatty acids; Monosodium phosphate derivatives of mono- and diglycerides of edible fats or oils, or edible fat-forming fatty acids; Propylene glycol; and mixtures thereof. Useful emulsifying agents may also include, for example, lecithin, calcium sterol, soy lecithin, monoglycerides, alkali stearates such as magnesium stearate and potassium stearate, sucrose ester, ethoxylated sorbitan esters (trade name: TWEEN such as TWEEN20 and TWEEN80), xanthum gum, guar gum, peptin, methyl cellulose, glycol esters such as propylene glycol ester, sorbitan esters such as sorbitan monostearate (trade name SPANS), glyceryl monostearate, tragacanth, sodium lauryl sulfate, sodium dioctyl sulfosuccinate, and mixtures thereof.

Generally, lecithin is a naturally occurring fatty substance or phospholipid, which could potentially be produced synthetically if desired. Lecithin may come from many sources, including both plant and animal tissues. Soybeans are the most common source of lecithin (soy lecithin), but other potential sources of lecithin include: eggs, animal tissues, milk, fish eggs, rapeseed, cotton seed and sunflower. One particularly preferable emulsifying agent is lecithin which is believed to act synergistically with mastic gum at certain proportions with respect to its use in equine animals. While not wishing to be bound to any particular theory one potential reason that soy lecithin may be particularly effective is that soy lecithin comprises phosphatidylethanolamines which are also found in the lipid bilayer of most cells.

A chemical formula for a lecithin is $C_8H_{17}O_5NRR'$ wherein R and R' are the same or different fatty acid groups. Pure lecithin is generally a phosphatidyl choline. That is, lecithins are mixtures of diglycerides of fatty acids linked to the choline ester of phosphoric acid. Thus, lecithins are often classed as phosphoglycerides or phosphatides (phospholipids). Commercially available lecithin is often a mixture of acetone insoluble phosphatides. For example, LECITHIN FCC, available from, for example, Spectrum Chemical, is a substance that is of a fatty nature and occurs naturally in animals and plant tissues. It is a brownish yellow color and contains a range of substances such as triglycerides, glycerol, phosphoric acid and so on. Other potential sources of lecithin useful in the present invention include, for example, Cargill.

The specific emulsifying agent such as lecithin and amounts employed in the supplements and method of treatment/prevention also vary depending upon a number of factors. Such factors include, for example, the desired results, the animal being treated as well as the types and amounts of other ingredients employed and the form of the supplement. So long as the emulsifying agent such as lecithin is capable of being mixed with the mastic gum, it may be in any form. Preferably, the emulsifying agent such as lecithin with mastic gum employed may be in a form such as granules, powders, or even liquid such that it may be substantially homogeneously mixed with the mastic gum. Suitable forms for the substantially homogeneous mixture include, for example, top dressings as described herein. Moreover, such mixtures include, for example, oral gels and "extruded treats". Oral gels may include, for example, a gel comprising the ingredients and amounts described herein or alternatively from at least about 1, 1.5, 2, 2.5, or 3 or more grams per dose with or without a time release component. Such gels may typically comprise less than about 6, 5, 4.5, 4, 3.5, or 3 or less grams per dose with or without a time release component.

"Extruded Treat" as used herein means a formulation in the form of, for example, a snack or other supplement to be provided at, for example, a non-routine feeding. Such extruded treats can comprise an appropriate amount of ingredients described herein or alternatively from at least about 0.5, 1, 1.5, 2, 2.5, or 3 or more grams per dose with or without a time release component. Such extruded treats may typically comprise less than about 6, 5, 4.5, 4, 3.5, or 3 or less grams per dose with or without a time release component. Often such extruded treats are made via extrusion and are in the form of a solid such as a chewable biscuit similar to MILK BONE dog treats.

Weight Ratios and Amounts of Mastic Gum and Emulsifying Agent Such as Lecithin Employed As described previously, the amounts of mastic gum and emulsifying agent such as lecithin employed vary depending upon a number of factors including, for example, the degree or severity, if any, of gastrointestinal distress, desired results, the animal being treated as well as the types and amounts of other ingredients employed and the form of the supplement. Other factors may include, for example, the activity level and/or diet of the animal.

Generally, the weight ratio of mastic gum to emulsifying agent such as lecithin is determined such that the weight ratio is effective to prevent and/or treat gastrointestinal distress in an animal by providing the animal with about one to two or three or even four supplements per day. In such cases, the weight ratio of mastic gum to emulsifying agent such as lecithin is a range from about 1:2500 to about 1:1.25, or from about 1:1000 to about 1:300, or from about 1:500 to about 1:100, or from about 1:10 to about 1:50 based on the total weight of mastic gum and emulsifying agent such as lecithin. In other embodiments, the ratio of mastic gum to emulsifying agent such as lecithin is a range from about 1:1 to about 1:100, or from about 1:10 to about 1:50, or from about 1:20 to about 1:40, or is a range from about 1:15 to about 1:35, or from about 0.5:40. to about 1.5:20.

Some embodiments may comprise the step of identifying an animal with ulcer conditions for treatment. A preferred embodiment also comprises the step of dosing an animal with the supplement for at least thirty days.

Supplement Form and Process of Making

The nutritionally supplement comprising lecithin, mastic gum and/or other ingredients is typically administered or provided orally to the animal in any convenient manner. The supplement may be formulated as a powder, paste, granule, liquid, gel, capsule, tablet or pellets. Various additives may be added to the supplement in order to achieve the desired physical form. In one embodiment, the supplement may be administered or provided as a top dressing on top of food at one or more regular daily feeding times. A top dress is typically a formulation that is a supplement form which encourages the animal to ingest the supplement voluntarily. That is, if the supplement is not in the form of a "top dressing", then the animal may move the supplement to the side, spit out the supplement, or refuse the feeding altogether.

The specific process of making the supplement, of course, will vary depending upon the final form desired, the specific ingredients and their form, amounts employed, and other factors. Generally, the process typically involves mixing the desired emulsifying agent such as lecithin and mastic gum at ambient conditions to form a substantially homogenous mixture. If other ingredients are desired in the supplement, then in most cases the ingredients may be mixed prior to, simultaneously or even after the emulsifying agent such as lecithin and mastic gum are mixed. In some cases, it may be desirable to add the desired amounts of emulsifying agent such as lecithin and mastic gum to an already commercially available supplement lacking sufficient amounts of lecithin and mastic gum. Once the desired ingredients are mixed, they may be put in the desired form, e.g., powder, paste, granule, liquid, gel, or pellets using techniques known to those skilled in the art.

Other Ingredients

Other ingredients may be added to the supplement so long as the ingredients do not substantially interfere with the desired effects of the supplement comprising mastic gum and emulsifying agent such as lecithin. In certain embodiments, the supplement may additionally comprise beneficial amounts of biotics such as probiotics and/or prebiotics, vitamins, minerals, and/or other nutritional supplements.

Probiotics are live "good" microorganisms, such as bacteria and yeast. Probiotics that may be useful in the supplement, particularly for equine supplements, include *Enterococcus faecium, Lactobacillus acidophilus, Lactobacillus caseii* and *Lactobacillus plantarum.*

Additional potential probiotics may include:

*Lactobacillus* species including, but not limited to, *L. rhamnosus, L. salivarius, L. paracasei, L. gasseri, L. reuteri, L. bulgaricus, L. brevis, L. brevis, L fermentum*, and *L. reuteri.*

*Bifidobacterium* species including, but not limited to, *B. bifidum, B. longum, B. infantis, B. breve*, and *B. lactis.*

*Bacillus* species including, but not limited to, *B. coagulans* and *B. subtillius.*

*Streptoccocus* species including, but not limited to, *S. salivarius, S. thermophilus, S. cremoris, S. faecium* and *S. infantis.*

Other useful species may include, but are not limited to, *Saccharomyces boulardii, Aspergillus oryzae, Saccharomyces cerevisiae*, and *Aspergillus niger.*

The amount of probiotic to include in the supplement varies depending upon, among other items, the type of probiotic, other ingredients, and desired results. Typically, an amount of probiotic is measured in colony forming units (CFU's) per dose. In many cases, from millions to even billions of CFUs of probiotic may be included in a given supplement. Typically, the amount of probiotic may be at least 500 million, preferably at least 1 billion, more preferably at least 2 billion, preferably at least 3 billion up to as much as 10 billion CFUs per dose of supplement. Certain embodiment may comprise at least 10 to 15 billion CFUS per dose of supplement.

Disclosed embodiments may comprise at least 500 million, preferably at least 1 billion, more preferably at least 2 billion, preferably at least 3 billion up to as much as 10 billion CFUs of each species of *Lactobacillus acidophilus, Lactobacillus plantarum, Lactobacillus casei,* and/or *Enterococcus faecium* per dose of supplement.

In contrast to probiotics, prebiotics are the foods that feed the probiotics. Examples of prebiotic that may be included, particularly in equine supplements, include fructooligosaccharides (FOS), xylooligosaccrarides (XOS), polydextrose, pectin and psyllium. Additional potential prebiotics include the following:

Larch arabinogalactin (LAG), resistant starch, beta-glucans, trans-galactooligosaccharide, inulin, oligofructose, gum arabic, chicory root, Jerusalem artichoke, dandelion greens, garlic, leek, onion, asparagus, wheat bran, wheat flour, and banana.

Prebiotics may include short-chain prebiotic with 2-8 links per saccharide molecule or longer-chain prebiotics with 9-64 links per saccharide molecule. Prebiotics may comprise any of the above in combination as in Oligofructose-Enriched Inulin (OEI).

Prebiotic food ingredients are generally not digested by horses or other animals. Instead, prebiotics are digested by desirable microorganisms and probiotics in the digestive system to increase or enhance the numbers and/or activity of the desirable microorganisms and/or probiotics. Thus, including both probiotics and prebiotics in the supplement may assist in further treating or preventing GI-related concerns, such as diarrhea, by facilitating the growth of the good microbes and/or minimizing the invasion and growth of disease-causing bacteria. Probiotics and/or prebiotics may be particularly preferable in supplements employed in animals such as horses that are on antibiotics or experiencing stress, transport, abrupt dietary changes, and/or *Clostridium* or *Salmonella* infections. Any of these may potentially alter the normal microbe population in, for example, a horse's large intestine.

If prebiotics are to be employed in the supplement, then the amount may vary widely depending upon, among other items, the type of prebiotic, other ingredients, and desired results. Typically, an amount of prebiotic is at least about 0.01, or at least about 0.1, or at least about 0.4 up to about 1, or up to about 2 grams per dose.

In addition to mastic gum, emulsifying agent such as lecithin, probiotics and prebiotics, a wide variety of vitamins, minerals, or other nutritional supplements may be included in the described nutritional supplement. Such other ingredients include, for example, B vitamins such as, for example, Vitamin B1 (thiamine) A coenzyme in the catabolism of sugars and amino acids; Vitamin B2 (riboflavin) A precursor of cofactors called FAD and FMN, which are needed for flavoprotein enzyme reactions, including activation of other vitamins; Vitamin B3 (niacin or nicotinic acid) A precursor of coenzymes called NAD and NADP, which are needed in many metabolic processes; Vitamin B5 (pantothenic acid) A precursor of coenzyme A and therefore needed to metabolize many molecules; Vitamin B6 (pyridoxine, pyridoxal, pyridoxamine) A coenzyme in many enzymatic reactions in metabolism; Vitamin B7 (biotin) A coenzyme for carboxylase enzymes, needed for synthesis of fatty acids and in gluconeogenesis; Vitamin B8 (inositol); Vitamin B9 (folic acid) A precursor needed to make, repair, and methylate DNA; a cofactor in various reactions; especially important in aiding rapid cell division and growth, such as in infancy and pregnancy; Vitamin B12 (various cobalamins; commonly cyanocobalamin or methylcobalamin in vitamin supplements) A coenzyme involved in the metabolism of every cell of the human body, especially affecting DNA synthesis and regulation, but also fatty acid metabolism and amino acid metabolism.

For certain embodiments, the ratio of total B-vitamins to mastic gum is from about 1:0.1 to about 1:4, or from about 1:0.3 to about 1:2, or from about 1:0.6 to about 1:1. B-vitamins may refer to all known B-vitamins including: thiamine, riboflavin, niacin, nicotinic acid, pantothenic acid, pyridoxine, pyridoxal, pyridoxamine, biotin, folic acid, folinic acid, cyanocobalamin, methylcobalamin or other cobalamins, choline, adenine, or carnitine, adenosine monophosphate (AMP), inositol, para-aminobenzoic acid, pterylhepta-glutamic acid, orotic acid, dimethyl glycine, L-carnitine, carnitine, and myo-inositol.

Other useful ingredients for the supplement may include DL methionine, Vitamin E, zinc, selenium, distillers dried grains with or without solubles, magnesium mica, corn distillers dried grains, wheat middlings, alfalfa meal, dehydrated alfalfa, rice mill by product, rye flour, beet pulp, dicalcium phosphate, flaxseed meal, oat flour, oat oil, magnesium stearate, cellulose, silicon dioxide, gelatin, maltodextrin, silica, fructose, inulin, inouline, soy protein isolate, rice bran, soybean flour, coconut meal, marine lipid concentrates, kelp, kaolin, and/or pectin.

If desired, formulation aids and/or flavoring aids may be employed in the supplement at useful amounts. Such ingredients include, for example, silicon dioxide, maltodextrin, vanilla flavor, and the like. Flavoring aids are typically added in a useful amount which encourages the animal to ingest the supplement voluntarily. Such aids include, for example, maltodextrin, vanilla flavor, and flavors such as fruit, vegetable, apple, honey, molasses, karo syrup, banana, citrus, orange, beet pulp, herbs, fenugreek, cherry, rosemary, cumin, carrot, peppermint, oregano, various flavors of jams and jellies. Suitable flavoring may be available at various suppliers including, for example, Agriflavors, Inc. Some embodiments may contain a pH buffer or alkalinizing agent. Alternative embodiments may contain an additive for coating the interior of an animal stomach. Still other embodiments may contain anti-fungal additives.

Chart 1 below shows a potential embodiment as well as potential dosage ranges for the disclosed supplement. Such a supplement would be particularly preferable for horses at a dose of about once daily for preventing gastrointestinal distress. If desired, the supplement could be administered in two or even three or more daily doses for treatment purposes depending upon the severity of the distress. In certain circumstances administering a dose every other day, every third day, or weekly may be appropriate depending on the nature and severity of the distress. Generally, each of the below ingredients with the exception of mastic gum and emulsifying agent such as lecithin are optional and thus need not be present at even the low level described in Chart 1 below. That said, it is often preferable to include at least the prebiotics and probiotics with the mastic gum and emulsifying agent such as lecithin.

If desired the composition may be formulated as a time release formulation. That is, the composition may further comprise on or more ingredients that facilitate release of the mastic gum in a controlled release over time. The skilled artisan will appreciate the type and amount of such ingredients as being used in conventional time release formulations. Such ingredients include, for example, methyl celluloses such as hydroxy methyl cellulose, hydroxy ethyl cellulose, and the like in amounts necessary to delay the release of the mastic gum for desired amounts of time.

If desired, an absorbent may be added to the formulation. Useful amounts of such absorbents may be useful to, for example, facilitate removal of heavy metals & toxins, balance pH levels, or both. Suitable absorbent may include micronized zeolites such as clinoptilolite. Often, such absorbents may attract positive minerals such as calcium, magnesium, potassium, sodium and iron. These common positive cations may then be displaced by heavy metals such as cadmium, mercury, nickel, and arsenic and removed safely from the body.

Chart 1:

|  | Formulation | Dose Amount Range Low | Dose Amount Range High |
|---|---|---|---|
| Mastic Gum | 1.00 gm | 0.02 gm | 4.00 gm |
| DL Methionine | 1.72 gm | 0.05 gm | 3.00 gm |
| Inositol | 368 mg | 100 mg | 550 mg |
| Niacin | 135 mg | 10 mg | 250 mg |
| Thiamine | 42 mg | 10 mg | 150 mg |
| Riboflavin | 38 mg | 10 mg | 75 mg |
| Pyridoxine | 20 mg | 5 mg | 30 mg |
| Biotin | 2 mg | 0.2 mg | 20 mg |
| Vitamin B12 | 184 mcg | 50 mcg | 500 mcg |
| Vitamin E | 123 mg | 30 mg | 250 mg |
| Zinc | 1% | 0.03% | 2% |
| Selenium | 40 ppm | 10 ppm | 100 ppm |
| FOS - Prebiotics | 0.5 gm | 0.01 gm | 2.0 gm |
| emulsifying agent (Soy Lecithin) | 28.7 gm | 5.0 gm | 200 gm (preferably up to 50 gm) |
| Probiotics | 3 billion CFU's | 500 million CFU's | 10 billion CFU's |
| Lactobacillus acidophilus, Lactobacillus plantarum, Lactobacillus casei, Enterococcus faecium | | | |
| Silicon Dioxide | 1% | .05% | 2% |
| Maltodextrin | 2.8% | 1% | 5% |

First Example Study Using the Formulation in Chart 1 Above in Quarter Horses Eight quarter horses, which were actively engaged in racing or race training, were examined. These horses were positively diagnosed with significant and differing levels of Equine Gastric Ulcer Syndrome (EGUS), gastric erosions or lesions in the stomach. The gastric ulcers or lesions were verified through endoscopies on all horses in the initial phase of the study. Inclusion criteria were horses specifically showing significant gastric ulceration and between the ages of 2-6 years. The significant gastric ulceration was confirmed by gastro scope and clinical observation. All horses selected were quarter horses in heavy training, most were young horses in race training.

The horses were all stalled and no changes in management occurred in the study time frame to confuse or affect the results of the study (i.e. horses removed from training, turned out to pasture or diet changes). These horses were all fed free choice Bermuda hay with a 14% sweet feed or Strategy as a grain source three times per day at three pounds each feeding. Additional supplementation included powder form electrolytes. None of the horses received any drug therapy thirty (30) days prior to start of the study or during the study.

Three horses were randomly selected to receive the supplement 3× per day (horse #5, #6 and #7). Five horses were randomly selected to receive the supplement 2× per day (horse #1, #2, #3, #4 and #8). The supplement provided was in a one (1) ounce dose as in Chart 1 above (reproduced below).

Supplement Given 3× Per Day or 2× Per Day

| | |
|---|---|
| Mastic Gum | 1.00 gm |
| DL Methionine | 1.72 gm |
| Inositol | 368 mg |
| Niacin | 135 mg |
| Thiamine | 42 mg |
| Riboflavin | 38 mg |
| Pyridoxine | 20 mg |
| Biotin | 2 mg |
| Vitamin B12 | 184 mcg |
| Vitamin E | 123 mg |
| Zinc | 1% |
| Selenium | 40 ppm |
| FOS - Prebiotics | 0.5 gm |
| Soy Lecithin | 28.7 gm |
| Probiotics | 3 billion CFU's |
| Lactobacillus acidophilus, Lactobacillus plantarum, Lactobacillus casei, Enterococcus faecium | |
| Silicon Dioxide | 1% |
| Maltodextrin | 2.8% |

After ten days of product supplementation, urine samples were collected from each horse and sent to an outside independent laboratory for testing. After a minimum of thirty (30) days, all horses were examined and endoscopies performed to evaluate product results.

All horses in the study showed good acceptance of the product, no side effects were reported and all horses tested negative for NSAIDS (non-steroidal anti-inflammatory drugs), Fluphenazine, Fluoetine and Reserpine. After thirty (30) days of supplementation, all horses, except one, showed significant improvement after the 2× or 3× daily supplements. The one horse that did not show improvement (Horse #8) was ultimately removed from the study due to the severity of the initial and ongoing ulcerations and need for comprehensive treatment. For the remaining seven horses, improvement was observed, positively verified and documented through endoscopies performed on all horses.

In less than 60 days on the product, Horse #7 had numerous Grade II and Grade III ulcers reduced to Grade I Ulcer and Hyperkeratosis. Horse #5 was diagnosed with Grade I and Grade II ulcers on 70% of the stomach wall. In less than 60 days on the product, this condition improved to Grade I ulcers and diffuse hyperkeratosis. Horse #7 initially showed numerous Grade II and Grade III ulcers and in a time period of just 30-60 days on the product, these ulcers were ultimately reduced to Grade I Ulcer and Hyperkeratosis. Horse #5 was initially diagnosed with Grade I and Grade II ulcers on 70% of the stomach wall. In only 30-60 days on the product, this condition improved and ultimately reduced to Grade I ulcers and diffuse hyperkeratosis.

Table 1 below shows the detailed assessments of the individual horses based on the initial gastroscope (positively diagnosing the severe ulceration) and the follow-up gastroscope documenting the results after product supplementation for 30-60 days.

TABLE 1

| HORSE | DAY 1 | DAY 30-60 |
|---|---|---|
| #1 4 yr. old QH stallion | Blister formation Hyperkeratosis Multiple Grade I ulcers | Hyperkeratosis Grade I ulcers on greater curvature of the stomach |
| #2 6 yr old QH gelding | Hyperkeratosis Grade II ulcers | Hyperkeratosis has improved Grade II ulcers remain |
| #3 2 yr. old QH gelding | Hyperkeratosis | Hyperkeratosis improved |
| #4 2 yr. old QH gelding | Grade I ulcers | Grade III ulceration present |
| #5 2 yr. old QH filly | Grade I and Grade II ulcers on 70% of stomach wall | Grade I ulcers, small in dameter Diffuse Hyperkeratosis |
| #6 3 yr. old QH gelding | Grade II and Grade III ulcers on lesser curvature of the stomach Greater curvature conctration and margo plicatis | Grade II and Grade III ulcers on margo plicatis Hyperkeratosis on greater curvature of the stomach |
| #7 2 yr. old QH gelding | Grade II and Grade III ulcers on greater curvature of the stomach | 1 - Grade I ulcer Hyperkeratosis Multiple superficial erosions |
| #8 2 yr old QH gelding | Hyperkeratosis on lesser curvature Grade II ulcers on 50% of greater curvature of the stomach | Marked Hyperkeratosis Grade I and Grade II ulcers on margo plicatis |

*horse #8 was ultimately removed from the study due to the severity of initial and ongoing ulcerations. Placed under care for comprehensive treatment.

The results of this study show the positive effects of utilizing this product in horses with severe gastric ulcers or lesions.

Terms and Definitions Used in the Example Study Above

Ulceration/Lesion Grading Scale:

| 0 | Normal |
|---|---|
| Grade I | Intact Mucosa with reddening or hyperkeratosis |
| Grade II | Mild ulceration - small single or multifocal lesions, mild hyperkeratosis |
| Grade III | Moderate ulceration - large single or extensive multifocal lesions |
| Grade IV | Severe ulceration - extensive lesions with areas of deep ulceration |

Hyperkeratosis—term often used in connection with lesions of the mucous membranes.

Margo Plicatus—cuticular ridge that separates the squamous mucosa from the glandular mucosa, in the equine stomach.

Recumbency—lying back or lying down, resting or leaning against something else.

Ulcer conditions should be understood to include various levels of Equine Gastric Ulcer Syndrome, gastric erosions, lesions in the stomach or other area of the digestive system in horses and other species.

Second Example Study in Quarter Horses

A second example study is being carried out in a similar manner to that of the first example above except that the horses were provided only one daily dose of the formulation listed in chart 1 above instead of the two or three daily doses in the first example study. Preliminary findings are below.

| HORSE | DAY 1 | DAY 7 | DAY 22 | DAY 30 |
|---|---|---|---|---|
| #9 | Small pin point ulcers under cardiac sphincter Grade I ulcers on greater | Resolving gastric ulcers Film stuck to wall - no ulcers | Exaggereted epithelium, no ulcer, Hyperkeratosis believed to be due to high, intesnsity, high stress rodeo event riding 8 hours per day just 4 days earlier | Lesser curvature Started hauling and working harder |

| HORSE | DAY 1 | DAY 23 | DAY 30 |
|---|---|---|---|
| #10 | Loose epithelium Hyperkeratosis | No sign of ulcers | No gastritis or ulcers |

-continued

| HORSE | DAY 1 | DAY 7 | DAY 10 | DAY 14 | DAY 30 |
|---|---|---|---|---|---|
| #11 | No ulcer Hyperkeratosis | No ulcer Hyperkeratosis | Hyperkeratosis and gastritis nearly gone | Hyperkeratosis but improved | Started hauling and working harder |

| HORSE | DAY 1 | DAY 7 | DAY 28 |
|---|---|---|---|
| #12 | No ulcer Hyperkeratosis | Coating over Hyperkeratosis No ulcers | No ulcers Very Mild Hyperkeratosis on greater curvature |

The terms, descriptions and examples used herein are set forth by way of illustration only and are not meant as limitations. Those skilled in the art will recognize that many variations are possible within the spirit and scope of the invention as defined in the following claims, and their equivalents, in which all terms are to be understood in their broadest possible sense unless otherwise indicated.

What is claimed is:

1. A nutritional supplement for prevention or treatment of gastrointestinal distress in animals comprising:
   an emulsified mastic gum;
   wherein the supplement is in the form of a pellet, powder, granule, liquid or gel, wherein the supplement is effective to prevent or treat gastrointestinal distress in an animal, and wherein the weight ratio of mastic gum to an emulsifying agent in the emulsified mastic gum is from about 1:10 to about 1:50 based on the total weight of emulsified mastic gum.

2. The supplement of claim 1, farther comprising one or more probiotics, one or more probiotics, or a combination thereof.

3. The supplement of claim 1, wherein the emulsified mastic gum comprises lecithin.

4. The supplement of claim 3, wherein the emulsified mastic gum comprises a weight ratio of mastic gum to lecithin wherein said weight ratio is effective to prevent or treat gastrointestinal distress in an animal by providing the animal with about one dose per day.

5. The supplement of claim 1, further comprising one or more B-vitamins, one or more minerals, or a combination thereof.

6. The supplement of claim 5, wherein the weight ratio of the one or More B-vitamins to mastic gum is from about 1:0.1 to about 1:4 based on the total weight of B-vitamins and mastic gum.

7. The supplement of claim 3, wherein the supplement is in the form of a pellet, powder, or gel.

8. The supplement of claim 1 wherein the supplement is an equine supplement and comprises from about 0.02 to about 4 grams of mastic gum, from about 5 to about 50 grams of lecithin, one or more B vitamins, one or more prebiotics or probiotics, and one or more minerals.

9. The supplement of claim 1, further comprising a pH buffer.

10. The supplement of claim 1 wherein the emulsified Mastic gum comprises an emulsifier selected from the group consisting of diacetyl tartaric acid esters of mono- and diglycerides of edible fats or oils, or edible fat-forming fatty acids; mono- and diglycerides of edible fats or oils, or edible fat-forming acids; monosodium phosphate derivatives of mono- and diglycerides of edible fats or oils, or edible fat-forming fatty acids; monosodium phosphate derivatives of mono- and diglycerides of edible fats or oils, or edible fin-forming fatty acids; propylene glycol; and mixtures thereof.

11. The supplement of claim 1 wherein the emulsified mastic gum comprises an emulsifier selected from the group consisting of a lecithin, calcium sterol, soy lecithin, a monoglyceride, magnesium stearate, potassium stearate, sucrose ester, an ethoxylated sorbitan ester, xanthum gum, guar gum, peptin, methyl cellulose, a glycol ester, a sorbitan ester, glyceryl monostearate, tragacanth, sodium lauryl sulfate, sodium dioctyl sulfosuccinate, and mixtures thereof.

* * * * *